United States Patent
Weisman et al.

(10) Patent No.: US 6,463,124 B1
(45) Date of Patent: Oct. 8, 2002

(54) MINIATURE ENERGY TRANSDUCER FOR EMITTING X-RAY RADIATION INCLUDING SCHOTTKY CATHODE

(75) Inventors: Effraim Weisman, Yuvalim; Nathan Sela, Modiin; Dan Hashimshony, Pardes-Hana; Uriel Halavee, Ramat Gan; Guy Shinar, Rehovot; Gilad Marcus, Jerusalem, all of (IL)

(73) Assignee: X-Technologies, Ltd., Orangeburg, NY (US)

( * ) Notice: Subject to any disclaimer, the term of this patent is extended or adjusted under 35 U.S.C. 154(b) by 169 days.

(21) Appl. No.: 09/596,530

(22) Filed: Jun. 19, 2000

Related U.S. Application Data

(63) Continuation-in-part of application No. 09/504,709, filed on Feb. 16, 2000, now abandoned, and a continuation-in-part of application No. 09/434,958, filed on Nov. 5, 1999, which is a continuation-in-part of application No. 09/325,703, filed on Jun. 3, 1999, now Pat. No. 6,324,257.
(60) Provisional application No. 60/087,970, filed on Jun. 4, 1998.

(51) Int. Cl.[7] .............................................. H01J 35/06
(52) U.S. Cl. ...................................... 378/136; 378/119
(58) Field of Search ........................ 378/65, 119, 121, 378/136

(56) References Cited

U.S. PATENT DOCUMENTS

| | | |
|---|---|---|
| 3,777,124 | 12/1973 | Pavkovich |
| 4,976,266 | 12/1990 | Huffman et al. ............ 128/659 |
| 5,090,043 | 2/1992 | Parker et al. ................ 378/121 |
| 5,153,900 | 10/1992 | Nomikos et al. ............. 378/65 |
| 5,199,054 | * 3/1993 | Adams et al. .............. 378/124 |
| 5,243,638 | 9/1993 | Wang et al. ................ 378/119 |

(List continued on next page.)

FOREIGN PATENT DOCUMENTS

| | | |
|---|---|---|
| EP | 0 860 180 A2 | 8/1998 |
| EP | 0 860 181 A2 | 8/1998 |
| EP | 0 860 180 A3 | 4/1999 |
| EP | 0 860 181 A3 | 4/1999 |
| WO | WO 97/07740 | 3/1997 |
| WO | WO 99/09580 | 2/1999 |
| WO | WO 99/36938 | 7/1999 |
| WO | WO 99/44687 | 9/1999 |
| WO | WO 99/45562 | 9/1999 |
| WO | WO 99/45563 | 9/1999 |

*Primary Examiner*—David P. Porta
(74) *Attorney, Agent, or Firm*—Rossi & Associates

(57) ABSTRACT

An apparatus provides in-situ radiation treating utilizing a miniature energy transducer to produce x-rays, wherein the energy transducer includes a Schottky cathode tip. More specifically, the energy transducer includes a transducer body, an anode provided at a first end of the transducer body, and a cathode provided at a second end of the transducer body opposite the anode. The energy transducer is coupled to an energy source by a flexible insertion device. The energy source provides electrical and/or light signals to the energy transducer via the flexible insertion device. Light transmitted from the energy source to the energy transducer by the flexible insertion device is focused on a Schottky cathode tip of the cathode by the optical fiber provided in the hollow core of the anode. The application of the light signal to the cathode tip results in heating of the tip and along with the electric field generated by the acceleration voltage it leads to electron Schottky emission and electron acceleration towards the anode. In another preferred embodiment, an electrical current, transmitted from the energy source to the energy transducer by the flexible insertion device, is applied to the Schottky cathode tip of the cathode, causing thermoemission. The electrons generated due to this process are accelerated towards the anode across a voltage difference between the anode and the cathode.

27 Claims, 3 Drawing Sheets

U.S. PATENT DOCUMENTS

| | | | |
|---|---|---|---|
| RE34,421 | 10/1993 | Parker et al. | 378/121 |
| 5,422,926 | 6/1995 | Smith et al. | 378/121 |
| 5,428,658 | 6/1995 | Oettinger et al. | 378/119 |
| 5,528,652 | 6/1996 | Smith et al. | 378/65 |
| 5,547,454 | 8/1996 | Horn et al. | |
| 5,566,221 | 10/1996 | Smith et al. | 378/145 |
| 5,621,780 | 4/1997 | Smith et al. | 378/65 |
| 5,729,583 | 3/1998 | Tang et al. | 378/122 |
| 5,854,822 | 12/1998 | Chornenky et al. | 378/122 |
| 5,910,102 | 6/1999 | Hastings | |
| 5,984,853 | 11/1999 | Smith | 600/1 |

\* cited by examiner

MINIATURE ENERGY TRANSDUCER FOR EMITTING X-RAY RADIATION INCLUDING SCHOTTKY CATHODE

CROSS-REFERENCE TO RELATED APPLICATIONS

This application is a continuation-in-part of Ser. No. 09/504,709 filed Feb. 16, 2000, now abandoned, and a continuation-in-part of, and claims priority from, U.S. patent application Ser. No. 09/434,958, filed Nov. 5, 1999, the contents of which are incorporated herein by reference, which in turn is a continuation-in-part application of U.S. patent application Ser. No. 09/325,703 filed Jun. 3, 1999, now U.S. Pat. No. 6,324,257 the contents of which are incorporated herein by reference, which in turn claims priority from Provisional Patent Application Ser. No. 60/087,970 filed Jun. 4, 1998.

FIELD OF THE INVENTION

The present invention relates to an apparatus and method for providing x-ray therapy in humans. More specifically, the present invention relates to an apparatus for providing in-situ radiation treatment that utilizes a miniature energy transducer to produce x-rays, wherein the energy transducer includes a Schottky cathode tip.

BACKGROUND OF THE INVENTION

Restenosis is a heart condition that afflicts 35%–50% of all people who undergo balloon angioplasty to improve blood flow in narrowed sclerotic arteries. The condition consists of a significant re-closing of the treated artery segment hours to several months after the procedure. As a result, the arterial lumen size is decreased and the blood flow downstream from the lesion site is impaired. Consequently, patients afflicted with restenosis must undergo an additional balloon angioplasty, and in some cases a coronary bypass surgery must be performed. Aside from the pain and suffering of these patients, recurrent stenosis is also a serious economic burden on society, with estimated expenses as high as 3.0 billion dollars per year in the United States economy alone.

Attempts to treat restenosis have been concentrated in both the pharmacological and medical device areas. While pharmacological solutions have been proven effective in treating only acute restenosis, a condition developing immediately after balloon angioplasty, some progress has been made with medical devices in the treatment of long term restenosis, a condition that develops up to a few months following balloon angioplasty. An example for such medical device is the stent. Stents can be inserted into an occluded artery to hold it open. Stents have been shown to prevent two of the three mechanisms that cause recurrent stenosis, namely, elastic recoil of the artery and negative remodeling of the arterial structure. The third mechanism, neointimal growth, consists of hyper-proliferation of smooth muscle cells from the lesion into the lumen and is not prevented by stents.

Ionizing radiation holds great promise for treating restenosis. Ionizing radiation serves to damage undesirable hyper-proliferating tissue and ultimately to prevent the hyper-proliferation of smooth muscle cells in the irradiated region. Research has shown that gamma and beta radiation delivered at the location of stenotic lesions effectively stop both animal and human intimal proliferation. The effective, yet non-hazardous, required dose to treat human restenosis is between seven and forty Gray (mjoule/gram), preferably a dosage greater than fifteen Gray measured two mm from the center of the radiation source, which penetrates the artery wall at a two mm depth over the lesion length.

In view of the above, various methods have been proposed to provide ionizing radiation treatment. For example, radiation catheters, based on the use of radioactive sources such as beta-emitting $^{32}P$, $^{90}Sr/^{90}Y$, $^{188}W/^{188}Re$, beta+ emitting $^{48}V$ or gamma emitting $^{192}Ir$, are at various stages of development and clinical evaluation. The radioactive sources, in a variety of configurations, are introduced to the treatment sites using special radiation catheters and the radioactive source is placed at the treatment site for a predetermined time period as to deliver the proper radiation dose. Radioactive stents are also used as alternative delivery means, composed of the above radioactive isotopes.

The gamma and beta radioactive sources used by the present radiation catheters and radioactive stents, however, have several drawbacks including a limited ability to provide selective control over the dose distribution or overall radiation intensity, and the logistical, regulatory, and procedural difficulties involved in dealing with radioactive materials. In addition, gamma-emitting devices jeopardize patients by exposing healthy organs to dangerous radiation during the introduction of the radiation source. Hospital personnel that handle radioactive materials are also at risk due to exposure. In addition to the risks these devices impose on patients, hospital staff, and the environment, use of these devices invokes a regulatory burden due to the need to comply with nuclear regulatory requirements.

An additional approach to providing ionizing radiation treatment is through the use of an x-ray emitting energy transducer, which is not radioactive. Conventional x-ray radiation for radiotherapy is produced by high-energy electrons generated and accelerated in a vacuum to impact a metal target. The x-ray emission is directly proportional to the electron beam current. However, the efficiency of x-ray generation is independent of electron current, but rather depends on the atomic number of the target material and on the acceleration voltage. Yet, another method for the production of x-rays is by direct conversion of light into x-ray radiation. It is known that the interaction of light with a target can produce highly energetic x-rays when the power densities achieved are in the range of $10^{16}$–$10^{17}$ watt/cm$^2$. With the development of femtosecond laser, such power densities are achievable with moderate size lasers (See C. Tillman et al, NIMS in Phys. Res. A394 (1997), 387–396 and U.S. Pat. No. 5,606,588 issued to Umstadter et al., the contents of each of which are incorporated herein by reference). A 100 femtosecond, one mJ laser pulse focused down to a 3 micron spot, for example, will reach this power density level.

A variety of medical applications of the direct laser light conversion method of x-ray generation are currently in the development stage. The direct laser light conversion method, for example, has been considered for medical imaging (See, Herrl in K et al. Radiology (USA), vol. 189, no. 1, pp. 65–8, Oct. 1993). Another medical application of femtosecond lasers is in improved non-thermal ablation of neural or eye tissue for surgical purposes (See, F. H. Loesel et al. Appl.Phys.B 66,121–128 (1998)). The development of compact table top models of femtosecond lasers makes laser generated x-rays an attractive alternative for radioactive material based radiotherapy.

Based on the above, an x-ray brachytherapy treatment apparatus and method has been developed. In x-ray brachytherapy an internal x-ray emitting miniature energy transducer generates x-rays in-situ. Co-pending and commonly assigned U.S. Pat. application Ser. No. 09/325,703 filed Jun. 3, 1999, and U.S. patent application Ser. No. 09/434,958 filed Nov. 5, 1999, describe miniaturized energy transducers that are coupled to flexible insertion devices to permit x-ray radiation treatment within the human body. Use of the miniaturized x-ray emitting energy transducer offers certain advantages with respect to intra vascular gamma and beta sources. These advantages are, but are not limited to, localization of radiation to the treatment site so that the treatment site may be irradiated with minimal damage to surrounding healthy tissue; reduction of hospital personnel risk due to exposure to radioactive materials; and minimization of the regulatory burden and additional costs that arise from the need to comply with nuclear regulatory requirements.

A variety of different types of cathode and anode structures have been proposed for the energy transducer. One proposal is to utilize a hollow cathode, which includes a cathode shell that defines a cavity. A light pulse is introduced into the cavity in order to heat an outer surface of the cathode shell, thereby causing thermionic emission of electrons from the outer surface. Another proposal for a hollow cathode incorporates the use of an electron escape nozzle, wherein an ion and electron plasma is generated in the cavity either by applying a light signal to an inner surface of the cathode shell or by providing a spark gap in the cavity of the conducting cathode shell. The electrons exit the cathode shell via the escape nozzle and are accelerated to the anode upon the application of a voltage pulse to the cathode. Still further, in a linear reverse cathode emission type of transducer, an anode is located at a first end of a transducer body and an emission element is located at a second end of the transducer body opposite the anode. The emission element is either a photoemission electron source or a thermionic emission surface, and generates electrons when activated by a light source.

One limitation that the different types of miniature energy transducers described in the above-cited references suffer from is imposed by their mode of operation, which involves the use of pulsed voltage. While replacing direct current (DC) voltage with pulse voltage increases the miniature x-ray transducer surface flashover threshold, thus enabling the manufacturing of smaller length devices, it holds some disadvantages. Pulsed voltage generators are more expensive, involve additional technological complexity and are less reliable when compared to DC voltage power suppliers. However, miniature x-ray transducers that are applied with a DC voltage in order to accelerate the emitted electrons from the cathode to the anode are facing efficiency problems. Taking into account the relatively low current density that can be produced with field emission cathodes supplied with DC voltage (in orders of milliamperes/mm$^2$ at most) it is questionable whether a miniature x-ray transducer with a cold cathode, can deliver the relevant x-ray dose for restenosis treatment. Miniature energy transducers that include a heated filament (thermionic) cathode also suffer from low electron generation efficiency while generating excessive heat.

One method to increase the current densities generated by miniature x-ray transducers supplied with DC voltage is the incorporation of both thermionic and field emission mechanisms in a single cathode. This type of emission is known as Schottky emission. Schottky emission is generated by heating a Schottky cathode tip to approximately 1,500° C. prior to its exposure to an electrical field created in the gap between a cathode and an anode. Providing thermal energy to the Schottky cathode tip increases the probability for electron emission due to "tunneling effect". This means that the probability of electrons replenished from the cathode surface to be accelerated towards the anode, following the voltage gradient to which they are exposed, is increased. Using a low work function material as an electron source further increases this probability. Thus, current densities obtained are orders of magnitude higher than with field emission mechanism alone (in orders of hundreds of milliamperes/mm$^2$), enabling the delivery of the relevant x-ray dose for restenosis treatment.

General information regarding Schottky cathode structures and Schottky emission can be found in the following references: C. H. Hinrichs, W. A. Mackie, P. A. Pincosy and P. Poulsen, "The Extended Schottky Cathode", IEEE Transactions On Electron Devices, Vol. 37, No. 12, December 1990, pp. 2575–2580, the contents of which is incorporated herein by reference; and L. W. Swanson and G. A. Schwind, "A Review of the ZrO/W Schottky Cathode" in "Handbook of Charged Particle Optics" by Jon Orloff (Editor), CRC Press, June 1997, pp.77–102, the contents of which is incorporated herein by reference.

Accordingly, it is an object of the present invention to provide a miniature energy transducer utilizing a Schottky cathode tip structure that combines both thermionic and field emission mechanisms in order to increase the current densities generated by the miniature energy transducer and provide the relevant therapeutic dose for restenosis treatment.

SUMMARY OF THE INVENTION

The present invention provides an apparatus for providing in-situ radiation treatment that utilizes a miniature energy transducer to produce x-rays, wherein the energy transducer includes a Schottky cathode. More specifically, the energy transducer includes a transducer body, an anode provided at a first end of the transducer body, and a cathode provided at a second end of the transducer body opposite the anode. The energy transducer is coupled to an energy source by a flexible insertion device. The energy source provides electrical and/or light signals to the energy transducer via the flexible insertion device. In one preferred embodiment, the anode includes a hollow central core, wherein an optical fiber is provided in the hollow central core. Light transmitted from the energy source to the energy transducer by the flexible insertion device is focused on a Schottky cathode tip of the cathode by the optical fiber provided in the hollow core of the anode. The application of the light signal to the cathode tip results in heating of the cathode and along with the electric field generated by the acceleration voltage it leads to electron Schottky emission and electron acceleration towards the anode. In another preferred embodiment, an electrical current, transmitted from the energy source to the energy transducer by the flexible insertion device, is applied to the Schottky cathode, causing thermo-emission. The electrons generated due to this process are accelerated towards the anode across a voltage difference between the anode and the cathode. The Schottky cathode tip is made from a low work function material, preferably selected from the group consisting of: tungsten, thoriated tungsten, lanthanum hexaboride, and zirconium oxide. The outer diameter of the energy transducer is 1.7 mm or less, while its length is preferably 7 mm or less and most preferably 3 mm or less.

Other advantages and features of the invention will become apparent from the following detailed description of the preferred embodiments and the accompanying drawings.

BRIEF DESCRIPTION OF THE DRAWINGS

The invention will now be described with reference to certain preferred embodiments thereof and the accompanying drawings, wherein.

DETAILED DESCRIPTION OF THE PREFERRED EMBODIMENTS

The present invention is particularly applicable to a system for the delivery of x-ray radiation to localized targets inside and outside the human body. Some therapeutic uses for the invention include the irradiation of coronary lesions to prevent restenosis, the treatment of tumors and of arteriovenous malformations. It will be understood, however, that the invention is not limited to these particular applications.

Figure 1:
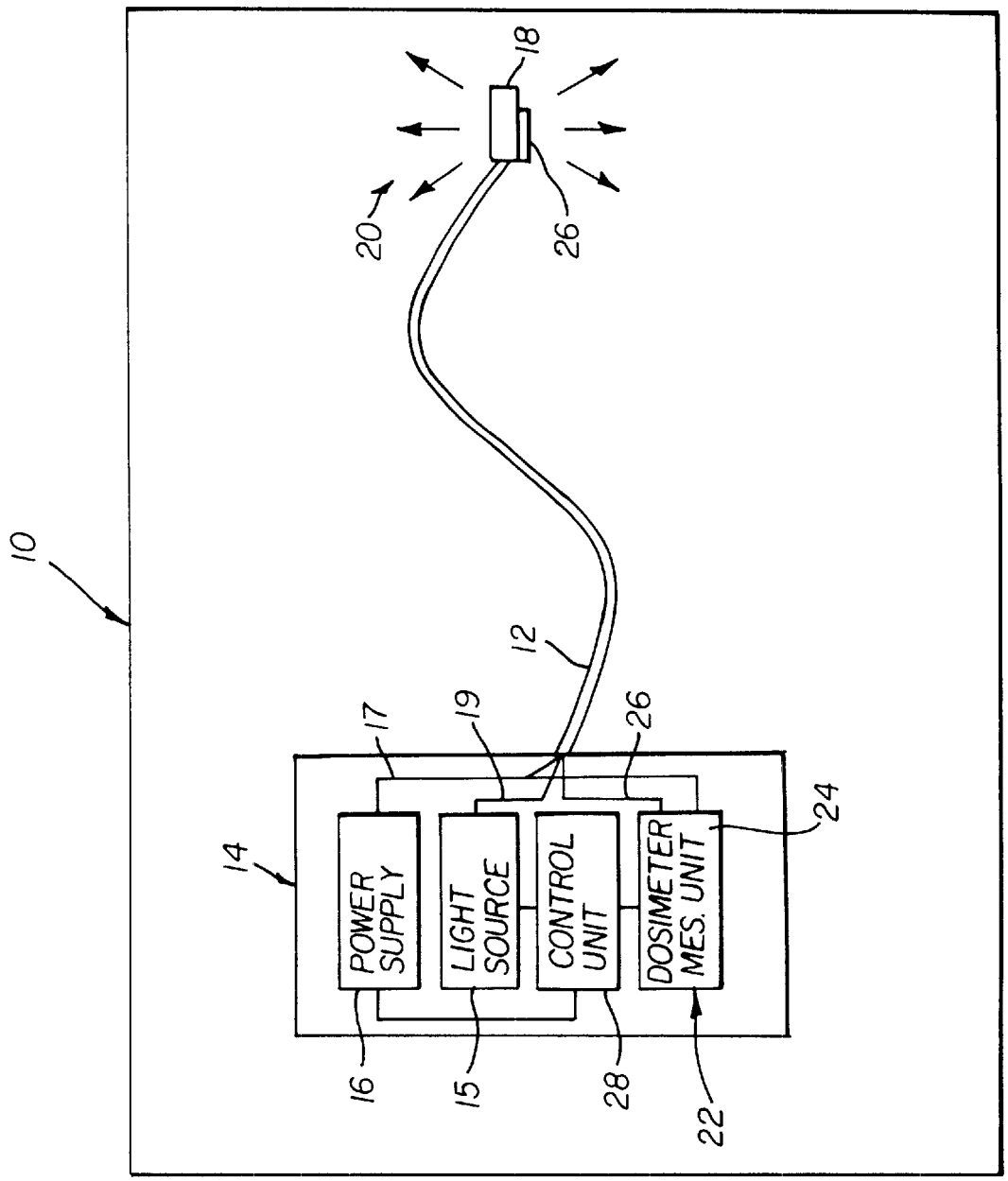
FIG. 1 is a functional block diagram of an x-ray radiation treatment system in accordance with the present invention.

FIG. 1 illustrates a x-ray radiation treatment system 10 in accordance with the present invention. The system 10 includes a miniature energy transducer 18 that is coupled to a distal end of the flexible insertion device 12. The flexible insertion device 12 delivers energy from an energy source 14 to the miniature energy transducer 18, which preferably converts electrical and/or optical signals received from the energy source 14 into x-ray radiation and distributes the x-ray photons (illustrated by arrows 20) in a predetermined distribution pattern. The energy source 14 is preferably located external to the patient, while the flexible insertion device 12 is manipulated to place the miniature energy transducer 18 in an area to be treated within the patient's body.

The miniature energy transducer 18 is preferably surrounded by x-ray transmissive insulation (not shown) that can be presented in direct contact with the human body. The transmissive insulation may be a material coated on an outer surface of the miniature energy transducer 18. Alternatively, the transmissive insulation may take the form of a capsule that encapsulates the miniature energy transducer 18. In any case, the miniature energy transducer 18 is preferably a relatively low-cost, replaceable and disposable unit. This avoids the necessity of complex sterilization processes required for instruments that are intended for multiple uses.

The system 10 may optionally further contain a dosimetery system 22, comprised of a dosimeter measurement unit 24 connected to a scintillating optical fiber 26. Preferably, the scintillating optical fiber 26 is a standard plastic scintillating optical fiber, containing embedded dopant atoms, which produce light photons upon being irradiated with x-ray photons. The distal end of the scintillating optical fiber 26 is located in the immediate vicinity of the miniaturized energy transducer 18. Preferably, the bulk of the length of the scintillating optical fiber 26 is housed within the flexible insertion device 12. The optional dosimeter measurement unit 24 is preferably housed within the energy source 14, and it is connected to a control unit 28, which is also housed within the energy source 14.

In general, the energy source 14 is adapted to provide electrical and/or optical signals through the flexible insertion device 12 that is correspondingly configured to deliver the energy to the miniature energy transducer 18. Accordingly, the energy source 14 is provided with a power supply 16, such as voltage generator, and/or a light source 15, for example a laser, respectively connected through an electrical conductor 17, preferably a coaxial cable, and an optical conductor 19 to the flexible insertion device 12. The control unit 28 directs the energy source 14 to deliver electrical and/or optical signals through the flexible insertion device 12 to the miniature energy transducer 18 as required by the operator. During x-ray treatment, the control unit 28 may also receive information from the optional dosimeter measurement unit 24 and may use this information to achieve the required dosage amount of radiation, providing the system with a feedback mechanism. Thus, the duration and amplitude of the energy supplied by the power supply 16 and optionally by the light source 15, as well as the total treatment time, may be varied to control the distribution of the x-ray radiation produced by the miniature energy transducer 18.

The flexible insertion device 12 preferably combines the electrical and the optional optical transmission lines into one structure, thus economizing the catheter diameter that must be preferably 1.7 mm or less, for coronary applications, and thereby allowing the flexible insertion device 12 to follow the contours of a blood vessel or any other body cavity.

Figure 2:
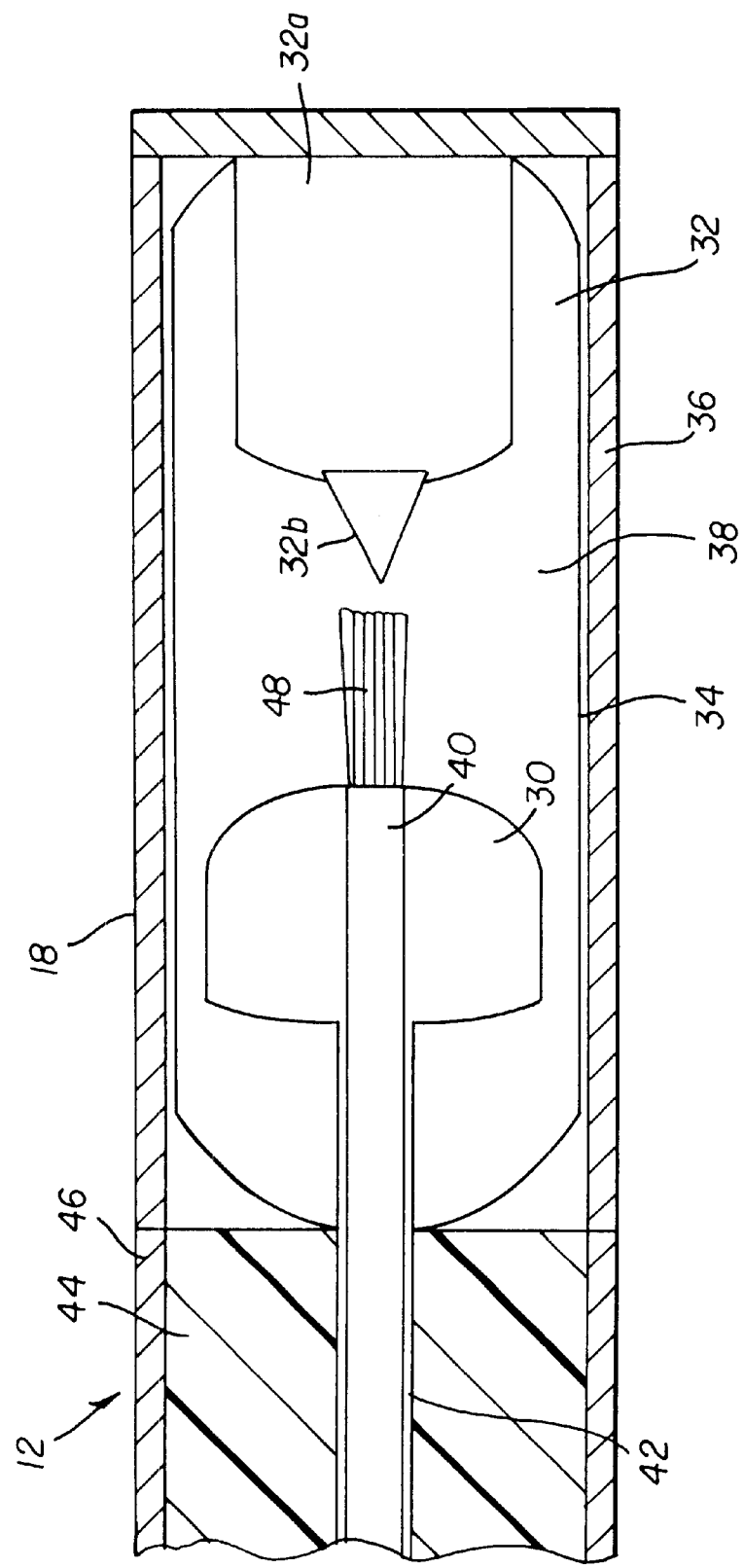
FIG. 2 is a cross-sectional view of an energy transducer in accordance with the invention that includes a Schottky cathode and a light source.

FIG. 2 illustrates a cross sectional view of the distal end of the flexible insertion device 12 and the energy transducer 18 of a preferred embodiment of the invention. The flexible insertion device 12 includes a central optical fiber 40, an inner electrical conductor 42 surrounded by an insulator 44, and an outer electrical conductor 46. The energy transducer 18 includes a Schottkey cathode 32 and an anode 30 that are separated by cavity 38 in which a vacuum is maintained. More specifically, the Schottkey cathode 32 preferably includes a [conductive] cathode base 32a, which can be made of any conductive material, and a Schottky cathode tip 32b. The optical fiber 40 extends through a hollow central core of the anode 30 and transmits light signals (illustrated by arrows 48) onto the Schottky cathode tip 32b of the cathode 32. The Schottky cathode tip 32b is made of a low work function material such as tungsten, thoriated tungsten, lanthanum hexaboride, or zirconium oxide. The anode 30 is preferably made of tungsten. The main body of the energy transducer 18 preferably includes an outer conductive layer 36 that electrically couples the cathode 32 to the outer electrical conductor 46 of the flexible insertion device 12 and an insulating shell 34 defining cavity 38 within an appropriate vacuum level is maintained. The energy transducer 18 preferably has a diameter of 1.7 mm or less, and a length less than 10 mm and most preferably 3 mm or less.

In operation, the Schottky cathode tip 32b is heated upon the application of a laser light signal received from the energy source 14. Electron emission commences once the temperature of the Schottky cathode tip 32b reaches approximately 1,500 C. in the presence of an applied voltage of 10–100 Kv. Although the voltage can be DC or variable, such as AC or pulsed voltage, preferably it is a DC voltage. Electrons emitted by the Schottky cathode 32 are accelerated across the voltage difference cavity 38 until they are decelerated upon impacting anode 30, which results in the generation of the required x-rays.

Figure 3:
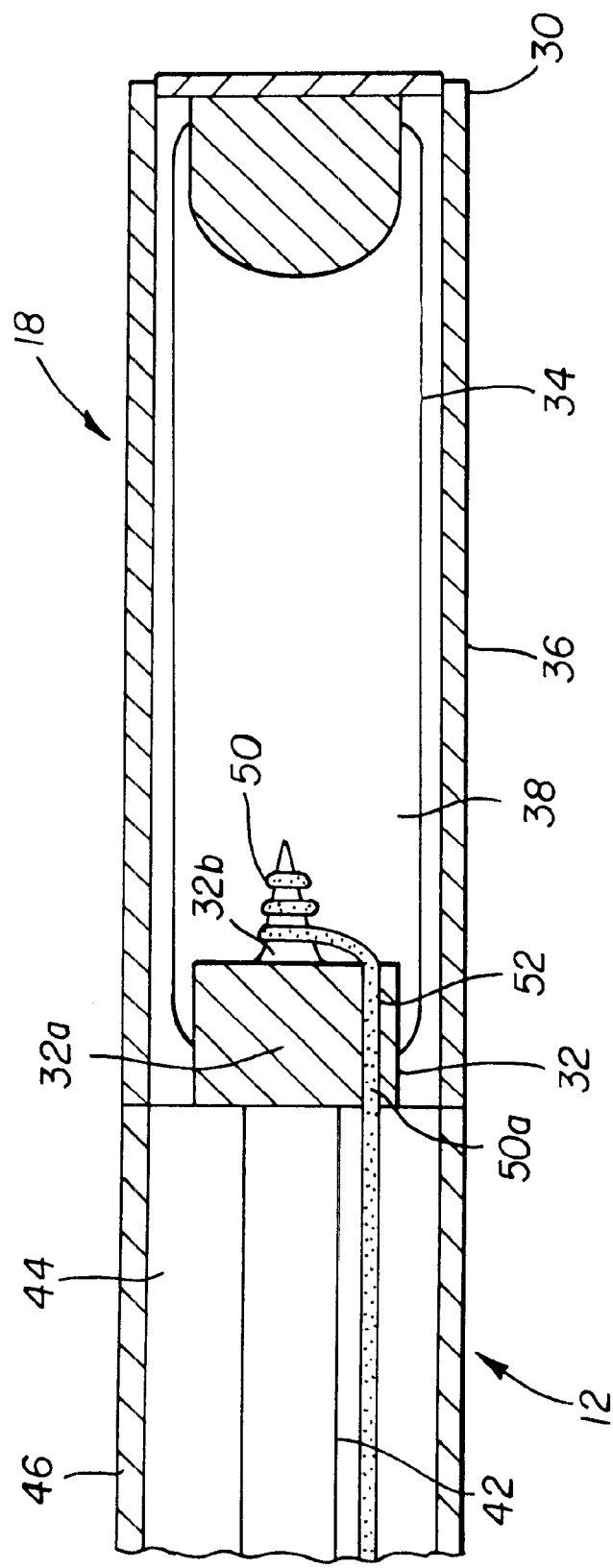
FIG. 3 is a cross-sectional view of an energy transducer in accordance with the invention that includes a Schottky cathode and an electrical current source.

FIG. 3 illustrates a cross sectional view of the distal end of the flexible insertion device 12 and the energy transducer 18 of another preferred embodiment of the invention. The flexible insertion device 12 includes an inner electrical conductor 42 surrounded by an insulator 44, and an outer electrical conductor 46. The energy transducer 18 includes a Schottkey cathode 32 and an anode 30 that are separated by cavity 38 in which a vacuum is maintained. The Schottkey cathode 32 preferably includes a cathode base 32a, which can be made of any conductive material, and a Schottky cathode tip 32b. The distal end of an electrical conducting wire 50, having a diameter of less than 200 microns, is coiled around the Schottky cathode tip 32b. The conducting wire 50 exits the energy transducer 18 via a hollow tunnel 52 inside the cathode base 32a, penetrates the insulator 44 of the flexible insertion device 12 and runs parallel and in close proximity to the inner electrical conductor 42. A segment 50a of the conducting wire 50, contained within the hollow tunnel 52, is separated from the cathode base 32a by a few microns of insulating material (not shown). Once the conducting wire 50 penetrates the insulator 44 of the flexible insertion device 12 it is separated from said conductor 42 by only a few microns of insulating material.

The proximal end of the conducting wire 50 is coupled to the power supply 16 through an electrical circuit (not shown), which is designed to maintain a constant voltage difference of approximately 5V between the conducting wire 50 and the inner electrical conductor 42 (or the cathode base 32a), thus preventing potential electrical bulk breakdown of the insulating material surrounding the conducting wire 50. In another preferred embodiment (not shown), the proximal end of the conducting wire 50 is coupled to a separate DC voltage supplier, which is housed within the energy source 14. The conducting wire 50 supplies an electrical current to the Schottky cathode tip 32b of the cathode 32, causing the heating of said tip 32b. The Schottky cathode tip 32b is made of a low work function material such as tungsten, thoriated tungsten, lanthanum hexaboride, or zirconium oxide. The anode 30 is preferably made of tungsten. The main body of the energy transducer 18 preferably includes an outer conductive layer 36 that electrically couples the cathode 32 to the outer electrical conductor 46 of the flexible insertion device 12 and an insulating shell 34 defining cavity 38 within an appropriate vacuum level is maintained. The energy transducer 18 preferably has a diameter of 1.7 mm or less, and a length less than 10 mm and most preferably 3 mm or less.

In operation, the Schottky cathode tip 32b is heated by the conduction of an electrical current induced by the DC voltage supplier through said tip 32b. Electron emission commences once the temperature of the Schottky cathode tip 32b reaches approximately 1,500 C. in the presence of an applied voltage of 10–100 Kv. Although the voltage can be DC or variable, such as AC or pulsed voltage, preferably it is a DC voltage. The voltage required for heating the Schottky cathode tip 32b is approximately 5V, thus in a preferred embodiment wherein a separate DC voltage supplier is used (not shown) a simple non-expensive supplier is needed for this operation. Electrons emitted by the Schottky cathode 32 are accelerated across the voltage difference cavity 38 until they are decelerated upon impacting anode 30, which results in the generation of the required x-rays.

The Schottky cathode tip 32b provides an effective electron source, which incorporates both thermionic and field emission mechanisms. The energy transducer 18 with the Schottky cathode tip 32b provides currents of several hundreds of microamperes when operated under moderate temperature conditions, about 1,500 C., and high electric fields, about 1,000,000 V/cm. The high electric field values are achieved due to the extremely small radius, about 1–10 microns at the distal end, of the Schottky cathode tip 32b. At the current levels described above, $10^{17}$ electrons are emitted at the cathode tip 32b after several minutes have elapsed. For example, acceleration of these electrons towards the anode under a potential difference of approximately 20 kV results in an x-ray production whose dose will be 15 Gray penetrating to a 2 mm depth within the artery wall, this radiation dosage takes into account the absorption of radiation in the tube confinement.

The combination of both thermionic and field emission mechanisms in one structure enables the production of the required dose, while exposing the energy transducer 18 to an electrical field of equal or even lower magnitudes, when compared to field emission cathode energy transducers or to hot filament cathode energy transducers. As a result, in a most preferred embodiment a relatively simple, inexpensive, reliable DC voltage generator can be used for the generation of the electrical field between the anode and the cathode. Furthermore, due to the relatively high currents of several hundreds of microamperes that are generated by the energy transducers disclosed within the present invention, the relevant therapeutic dose for restenosis treatment can be delivered, while it is questionable whether said relevant therapeutic dose can be delivered by field emission cathode energy transducers or hot filament cathode energy transducers alone.

The invention has been described with reference to certain preferred embodiments thereof. It will be understood, however, that modifications and variations are possible within the scope of the appended claims.

What is claimed is:

1. An x-ray emitting energy transducer comprising:
   a transducer body;
   an anode provided at a first end of the transducer body; and
   a Schottkey cathode provided at a second end of the transducer body opposite said anode;
   wherein a cavity is provided between said anode and said cathode; and
   wherein the outer diameter of the energy transducer is 1.7 mm or less.

2. An x-ray emitting energy transducer as claimed in claim 1, further comprising means for heating said Schottkey cathode, and means for applying a voltage across said anode and said cathode to generate an electric field within said cavity.

3. An x-ray emitting energy transducer comprising:
   a transducer body;
   an anode provided at a first end of the transducer body;
   a Schottkey cathode provided at a second end of the transducer body opposite said anode,
   wherein a cavity is provided between said anode and said cathode;
   means for heating said Schottkey cathode; and
   means for applying a voltage across said anode and said cathode to generate an electric field within said cavity;
   wherein said means for heating said Schottkey cathode applies light energy to said Schottkey cathode.

4. An x-ray emitting energy transducer comprising:
   a transducer body;
   an anode provided at a first end of the transducer body;
   a Schottkey cathode provided at a second end of the transducer body opposite said anode,
   wherein a cavity is provided between said anode and said cathode;
   means for heating said Schottkey cathode; and
   means for applying a voltage across said anode and said cathode to generate an electric field within said cavity;

wherein said means for heating said Schottkey cathode includes an optical fiber provided in a hollow central core of said anode.

5. An x-ray emitting energy transducer as claimed in claim 2, wherein said means for heating said Schottkey cathode applies an electrical current to said Schottkey cathode.

6. An x-ray emitting energy transducer as claimed in claim 5, wherein said Schottkey cathode includes a cathode base and a cathode tip, and wherein said means for heating includes an electrical conductor in contact with said cathode tip.

7. An x-ray emitting energy transducer as claimed in claim 6, wherein the electrical conductor passes through said cathode base.

8. An x-ray emitting energy transducer as claimed in claim 2, wherein said means for applying a voltage includes a first electrical conductor connected to said anode and a second electrical conductor connected to said cathode.

9. An x-ray emitting energy transducer as claimed in claim 8, wherein the transducer body includes an insulating shell and an outer conducting layer, comprising said second electrical conductor, formed on the insulating shell.

10. An x-ray emitting energy transducer as claimed in claim 1, wherein the cathode tip comprises a low work function material.

11. An x-ray emitting energy transducer as claimed in claim 10, wherein the cathode tip comprises at least one of tungsten, thoriated tungsten, lanthanum hexaboride, and zirconium oxide.

12. An x-ray emitting energy transducer comprising:
a transducer body;
an anode provided at a first end of the transducer body; and
a Schottkey cathode provided at a second end of the transducer body opposite said anode;
wherein a cavity is provided between said anode and said cathode; and
wherein the length of the energy transducer is 7 mm or less.

13. An x-ray emitting energy transducer as claimed in claim 12, wherein the length of the energy transducer is 3 mm or less.

14. An x-ray radiation treatment system comprising:
a flexible insertion device;
an x-ray emitting energy transducer coupled to a distal end of the flexible insertion device, wherein the x-ray emitting energy transducer includes a transducer body, an anode provided at a first end of the transducer body, and a Schottkey cathode provided at a second end of the transducer body opposite said anode, wherein a cavity is provided between said anode and said cathode;
an energy source coupled to a proximal end of the flexible insertion device.

15. An x-ray radiation treatment system as claimed in claim 14, further comprising means for heating said Schottkey cathode, and means for applying a voltage across said anode and said cathode to generate an electric field within said cavity.

16. An x-ray radiation treatment system as claimed in claim 15, wherein said means for heating said Schottkey cathode applies light energy to said Schottkey cathode.

17. An x-ray radiation treatment system as claimed in claim 15, wherein said means for heating said Schottkey cathode includes an optical fiber provided in a hollow central core of said anode.

18. An x-ray radiation treatment system as claimed in claim 15, wherein said means for heating said Schottkey cathode applies an electrical current to said Schottkey cathode.

19. An x-ray radiation treatment system as claimed in claim 18, wherein said Schottkey cathode includes a cathode base and a cathode tip, and wherein said means for heating includes an electrical conductor in contact with said cathode tip.

20. An x-ray radiation treatment system as claimed in claim 19, wherein the electrical conductor passes through said cathode base.

21. An x-ray radiation treatment system as claimed in claim 15, wherein said means for applying a voltage includes a first electrical conductor connected to said anode and a second electrical conductor connected to said cathode.

22. An x-ray radiation treatment system as claimed in claim 21, wherein the transducer body includes an insulating shell and an outer conducting layer, comprising said second electrical conductor, formed on the insulating shell.

23. An x-ray radiation treatment system as claimed in claim 14, wherein the cathode tip comprises a low work function material.

24. An x-ray radiation treatment system as claimed in claim 23, wherein the cathode tip comprises at least one of tungsten, thoriated tungsten, lanthanum hexaboride, and zirconium oxide.

25. An x-ray radiation treatment system as claimed in claim 14, wherein the outer diameter of the energy transducer is 1.7 mm or less.

26. An x-ray radiation treatment system as claimed in claim 14, wherein the length of the energy transducer is 7 mm or less.

27. An x-ray radiation treatment system as claimed in claim 26, wherein the length of the energy transducer is 3 mm or less.

* * * * *